US00PP31533P3

(12) United States Plant Patent
Couturieux

(10) Patent No.: US PP31,533 P3
(45) Date of Patent: Mar. 10, 2020

(54) ***HYDRANGEA* PLANT NAMED 'COUMONT'**

(50) Latin Name: *Hydrangea serrata x macrophylla*
Varietal Denomination: COUMONT

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 16/350,497

(22) Filed: Nov. 19, 2018

(65) Prior Publication Data

US 2019/0230835 P1 Jul. 25, 2019

(30) Foreign Application Priority Data

Jan. 19, 2018 (QZ) ..... PBR 2018/00121

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./226, 250
See application file for complete search history.

(56) References Cited

PUBLICATIONS

Floral Daily: Novelties at Plantarium 2017. https://www.floraldaily.com/article/9011274/novelties-at-plantarium-2017/. 4 pages. (Year: 2017).*

* cited by examiner

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Hydrangea* cultivar named 'COUMONT' is disclosed, characterized mophead inflorescences composed of yellow-green and pink flowers. Plants flower abundantly on same year's growth. Inflorescences and individual flowers hold up well in the rain and plants tolerate both full sun and partial shade. Plants are compact, well-branched and have large foliage. The new variety is a *Hydrangea*, normally produced as an ornamental plant for containers or gardens.

2 Drawing Sheets

Figure 1:
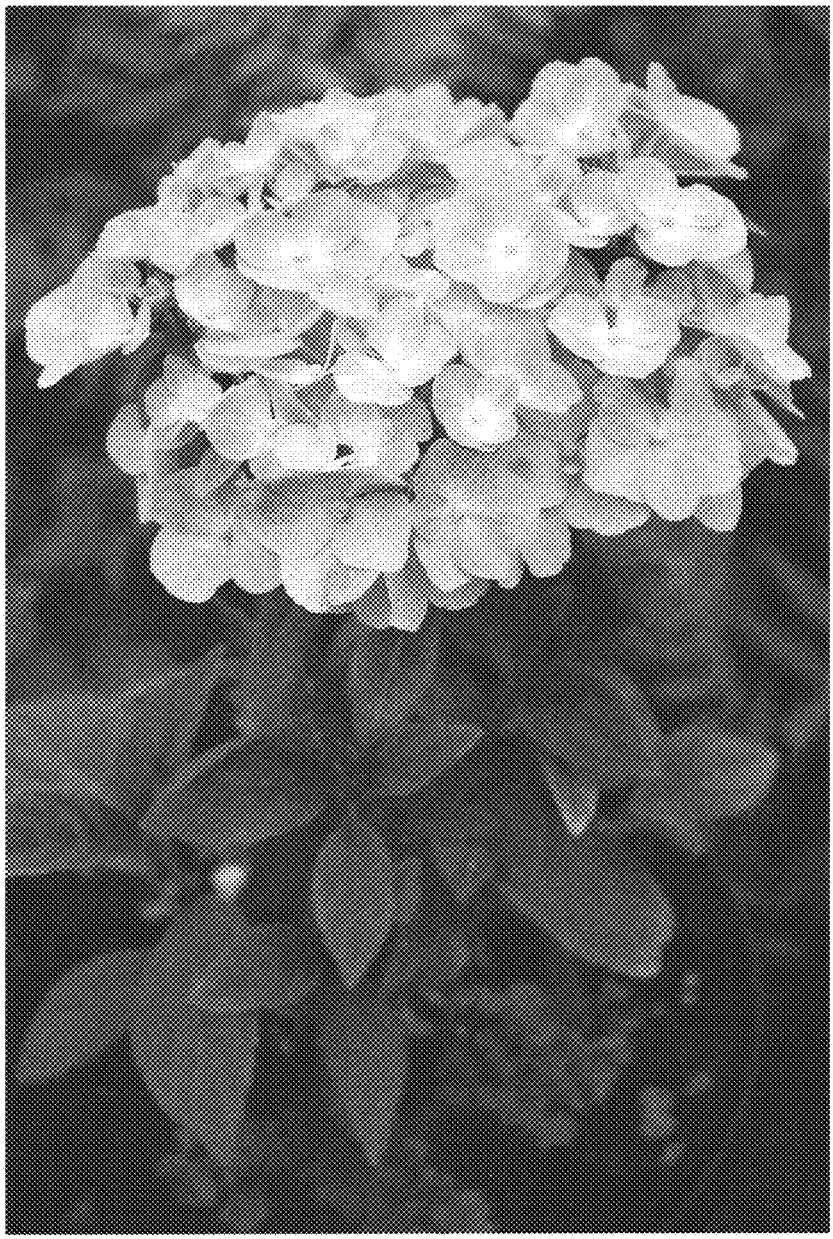

Latin name of the genus and species: *Hydrangea serrata* x *macrophylla*.
Variety denomination: 'COUMONT'.

BACKGROUND OF THE INVENTION

The present invention comprises a new and distinct *Hydrangea* cultivar hereinafter referred to by the cultivar name 'COUMONT'. This new *Hydrangea* was developed through a breeding program in Moyenmoutier, France. 'COUMONT' was selected from a population of seedlings that resulted from a cross of the seed parent, *Hydrangea serrata* 'Santiago', U.S. Plant Pat. No. 22,070, and pollen parent *Hydrangea macrophylla* 'The Bride', unpatented.

The new cultivar was discovered by the inventor in Moyenmoutier, France in 2010. The inventor observed this interesting plant over several years, noting the exceptionally dense flowerheads and later the bronze coloration of the Fall foliage.

Asexual reproduction of the new cultivar 'COUMONT' by softwood cuttings was first performed during the May of 2012, at commercial nursery in Moyenmoutier, France. Subsequent propagation has shown that the unique features of this cultivar are stable and reproduced true to type in successive generations.

SUMMARY OF THE INVENTION

The cultivar 'COUMONT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COUMONT' These characteristics in combination distinguish 'COUMONT' as a new and distinct *Hydrangea* cultivar:

1. Mophead inflorescences, in the shape of a half ball colored pink and light green.
2. The flowers hold up well in the rain.
3. The foliage is large, plants compact and well branched.
4. Very hardy to cold when grown in flower pots.
5. Tolerance for both full sun and partial shade.
6. Long lasting inflorescence suitable for cut flowers.
7. Abundant flowering on same year's growth.

PARENT COMPARISON

Plants of 'COUMONT' are similar to plants of the seed parent in most horticultural characteristics, however, plants of the new cultivar 'COUMONT' differ in the following:

1. Inflorescences of 'COUMONT' are mophead, inflorescences of 'Santiago' are lacecap.
2. Plants of the new variety produce more branches than plants of 'Santiago'.

Plants of 'COUMONT' are similar to plants of the pollen parent in most horticultural characteristics, however, plants of the new cultivar 'COUMONT' differ in the following:

1. Flowers of 'COUMONT' are colored yellow-green and pink, flowers of 'The Bride' are white.

COMMERCIAL COMPARISON

Plants of 'COUMONT' are similar to plants of *Hydrangea* 'Bouquet Rose', unpatented, in most horticultural characteristics, however, plants of the new cultivar 'COUMONT' differ in the following:

1. Plants of the new variety are more compact than plants of this comparator.
2. Sepals of this comparator are serrate, sepals of 'COUMONT' are entire.
3. Sepal coloration of this comparator are significantly different shades of pink 'COUMONT' can also be compared to the unpatented commercial variety *Hydrangea* 'Messalina'. These varieties are similar in most horticultural characteristics, however 'COUMONT' differs in the following:

1. The new variety has a lighter pink sepal color than this comparator.
2. Bluing treatment is impossible with the new variety; bluing treatment is possible with this comparator.
3. Inflorescences of this comparator are lacecap, inflorescences of 'COUMONT' are mophead.

BRIEF DESCRIPTION OF THE PHOTOGRAPHS

The accompanying photograph in FIG. 1 illustrates a mature inflorescence on a flowering plant of 'COUMONT' grown in outdoors in Vosges, France.

Figure 2:
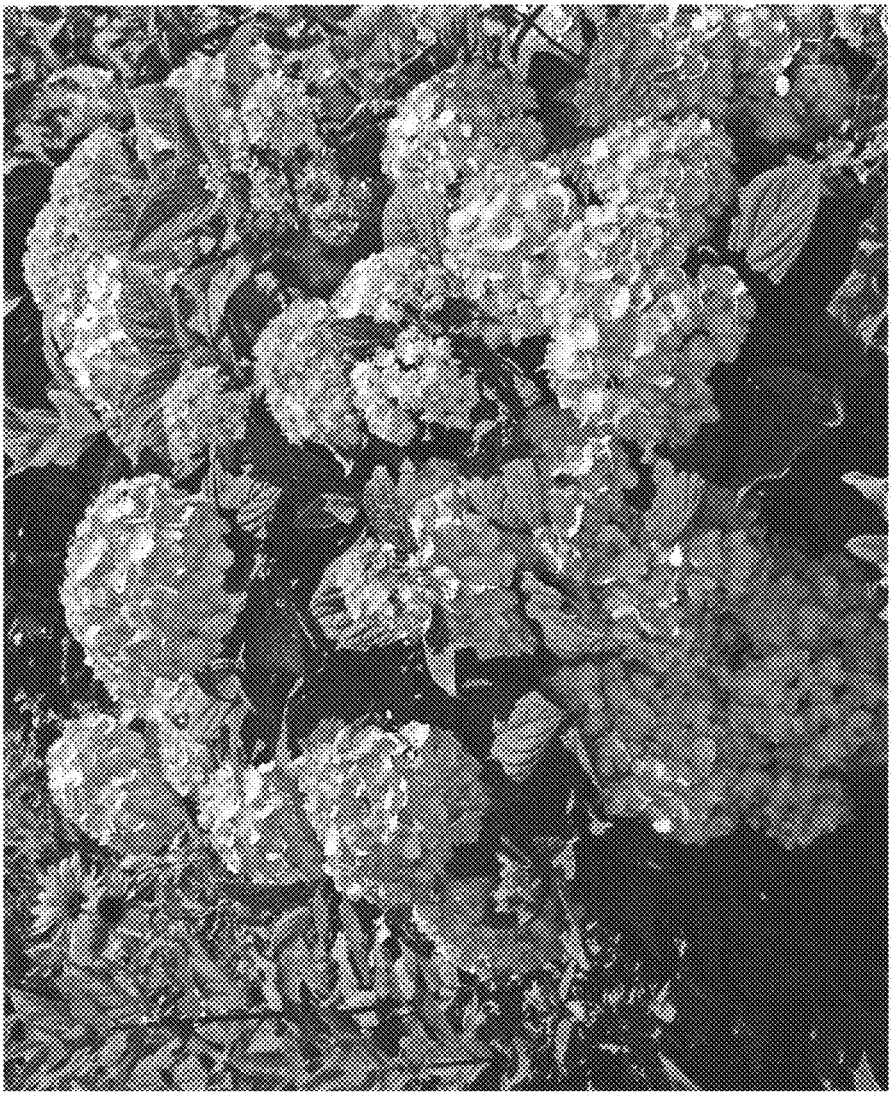

FIG. 2. illustrates in full color a flowering plant of 'COUMONT' having inflorescence at various stages of maturity. Age of the plant photographed is approximately 2-3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The 2007 Royal Horticultural Society Colour Chart except where general terms of ordinary dictionary significance are used. The following observations and measurements describe 'COUMONT' plants outdoors, in Vosges, France. The growing temperature ranged from approximately 18° C. to 27° C. daytime and 5° to 10° C. at night. Measurements and numerical values represent averages of typical plant types. Measurements were taken during October of 2012.

Botanical classification: *Hydrangea macrophylla* 'COUMONT'.

PROPAGATION

Time to initiate roots: Approximately 18 days at approximately 27° C.

Time to produce a rooted young plant: Approximately 60 days at approximately 27° C.

Root description: Thick and fine, freely root branching and dense, fibrous. Color is white and brown, not accurately measured with an R.H.S. chart.

Propagation method: Softwood cuttings.

PLANT

Age of plant described: About 2 years.

Growth habit: Flowering, deciduous perennial shrub.

Overall plant shape: Compact, globular.

Height: 120 to 150 cm.

Plant spread: 100 to 120 cm.

Growth rate: Rapid.

Plant vigor: Very strong.

Branching characteristics: Well branched, above average for a *H. macrophylla.*

Length of lateral branches: 40 to 100 cm.

Diameter of lateral branches: 8 to 15 mm.

Lateral branch shape: Round.

Fasciation: Stem fasciation not present.

Lateral branch strength: Strong and resistant to environmental stressors such as wind and rain.

Branch color: Near Green 143C.

Branch angle: Average range 20 to 65° from center.

FOLIAGE

Leaf:

*Arrangement.*—Opposite.

*Shape of blade.*—Ovate.

*Apex.*—Acute.

*Base.*—Rounded.

*Margin.*—Crenate.

*Texture and appearance of top surface.*—Pubescence, somewhat hirsute.

*Texture and appearance of bottom surface.*—Lightly pubescent.

*Color.*—Young foliage upper side: Near RHS Green 141B. Young foliage under side: Yellow-Green N144B. Mature foliage upper side: Near RHS Green 141B. Mature foliage under side: Yellow-Green 144B. Fall foliage upper side: Near RHS Yellow-Green 146A marbled Greyed-Orange N167A and N167C. Fall foliage under side: Near RHS Yellow-Green 146B marbled Greyed-Orange N167C.

*Venation.*—Type: Pinnate. Venation color upper side: Near RHS 141B. Venation color under side: Yellow-Green 144C.

Petiole:

*Average length.*—1 cm.

*Diameter.*—5 mm.

*Color.*—Upper side: Near Green 141C. Under side: Near Green 141C.

*Texture upper side.*—Glabrous.

*Texture under side.*—Glabrous.

FLOWER

Bloom period:

*Natural season.*—June to September, in France.

Inflorescence:

*Type.*—Mophead.

*Inflorescence shape.*—Globular.

*Weight.*—10 to 15 cm.

*Diameter.*—10 to 15 cm.

*Quantity of flowers per inflorescence.*—Average 50 to 60 sterile flowers.

*Persistent or self-cleaning.*—Persistent.

*Fragrance.*—None.

Sterile flower:

*Bud shape*.—Globular.

*Bud length*.—7 mm.

*Bud diameter*.—5 mm.

*Bud color*.—Near Red 55C.

*Flower aspect*.—Mainly flat, slightly upwardly cupped.

*Flower diameter*.—2 to 2.8 cm.

*Flower depth*.—1 to 1.3 cm.

Sterile flower sepals:

*Sepal arrangement*.—Single, overlapping.

*Sepal number*.—5.

*Length of sepal*.—8 to 15 mm.

*Width of sepal*.—About 10 mm.

*Apex*.—Broad acute.

*Shape of sepal*.—Obovate.

*Sepal margin*.—Entire.

*Sepal base*.—Broad attenuate.

*Sepal texture*.—Glabrous all surfaces.

Sepal color:

*Upper surface at first opening*.—Near RHS Yellow-Green 150C, blotched Green 143C. With some maturity, Red-Purple 68D, base and veins Yellow-Green 150D.

*Upper surface at maturity*.—Near RHS Red-Purple 65C, White 155C at base. Some veins near White 155C.

*Under surface at first opening*.—Near RHS Yellow-Green 150C, blotched Green 143C.

*Under surface at maturity*.—Near RHS Red-Purple 65C, veins near White 155C.

*Color when fading*.—Upper surface near Purple 75C, base Green-White 157A. Lower surface near Purple 75C.

Sterile flower pedicel:

*Length*.—3 to 7 mm.

*Diameter*.—About 2 mm.

*Angle*.—0 to 15° from center.

*Strength*.—Strong.

*Texture*.—Glabrous.

*Color*.—Near Yellow-Green 149D.

Fertile flower: Not observed to date.

REPRODUCTIVE ORGANS

Sterile flower: Not observed to date.

OTHER CHARACTERISTICS

Disease resistance: Neither resistance nor susceptibility to diseases or pests has been observed in this variety.

Temperature tolerance: USDA Zones 5 through 9. No tolerance for drought.

Fruit/seed production: Seed production not observed to date.

What is claimed is:

1. A new and distinct cultivar of *Hydrangea* plant named 'COUMONT' as herein illustrated and described.

* * * * *